United States Patent
Kush et al.

(10) Patent No.: US 9,046,497 B2
(45) Date of Patent: Jun. 2, 2015

(54) INTELLIGENT AIRFOIL COMPONENT GRAIN DEFECT INSPECTION

(75) Inventors: Matthew T. Kush, Martinsville, IN (US); Kong Ma, Carmel, IN (US); Robert Moriarty, Greenwood, IN (US)

(73) Assignee: Rolls-Royce Corporation, Indianapolis, IN (US)

( * ) Notice: Subject to any disclaimer, the term of this patent is extended or adjusted under 35 U.S.C. 154(b) by 593 days.

(21) Appl. No.: 13/416,516

(22) Filed: Mar. 9, 2012

(65) Prior Publication Data

US 2012/0232841 A1 Sep. 13, 2012

Related U.S. Application Data (60) Provisional application No. 61/451,038, filed on Mar. 9, 2011.

(51) Int. Cl.
| | | |
|---|---|---|
| *G06F 15/00* | (2006.01) | |
| *G01B 11/24* | (2006.01) | |
| *G01N 21/88* | (2006.01) | |
| *G01N 23/00* | (2006.01) | |

(52) U.S. Cl.
CPC ............ *G01N 21/8851* (2013.01); *G01N 23/00* (2013.01); *G01N 2021/8887* (2013.01)

(58) Field of Classification Search
CPC ................... G01N 21/8851; G01N 2021/8887
USPC ................ 702/167; 369/44.29, 44.34, 44.35; 378/58
See application file for complete search history.

(56) References Cited

U.S. PATENT DOCUMENTS

| | | | | |
|---|---|---|---|---|
| 5,149,978 | A * | 9/1992 | Opsal et al. .............. 250/559.19 |
| 5,615,003 | A * | 3/1997 | Hermary et al. ............ 356/3.03 |
| 5,815,198 | A * | 9/1998 | Vachtsevanos et al. ......... 348/88 |
| 5,962,853 | A * | 10/1999 | Huth-Fehre et al. ..... 250/339.11 |
| 6,229,872 | B1 * | 5/2001 | Amos ........................... 378/58 |
| 6,290,784 | B1 * | 9/2001 | Yasuhara et al. .............. 148/320 |
| 6,526,008 | B1 * | 2/2003 | Caponetto et al. ......... 369/44.35 |
| 6,703,633 | B2 * | 3/2004 | Tullis ........................... 250/556 |
| 7,397,550 | B2 * | 7/2008 | Hackney et al. ........... 356/237.1 |
| 8,222,126 | B2 * | 7/2012 | Tanaka et al. ................. 438/487 |
| 8,349,080 | B1 * | 1/2013 | Price ............................ 117/220 |
| 8,398,725 | B2 * | 3/2013 | Tanaka et al. ................ 29/25.01 |
| 2002/0054694 | A1 * | 5/2002 | Vachtsevanos et al. ....... 382/111 |
| 2002/0128790 | A1 | 9/2002 | Woodmansee |
| 2002/0159560 | A1 * | 10/2002 | Nienaber et al. ................ 378/81 |

(Continued)

FOREIGN PATENT DOCUMENTS

EP    1017044 A1 *  7/2000

OTHER PUBLICATIONS

International Search Report and Written Opinion, ISA/US, PCT/US2012/028493, Rolls-Royce Corporation, Jun. 12, 2012.

*Primary Examiner* — Carol S Tsai
(74) *Attorney, Agent, or Firm* — Shumaker & Sieffert, P.A.

(57) ABSTRACT

A system including a positioning system with a component manipulator structured to position a component in response to a positioning algorithm; a scanning system capable of producing a set of light waves directed at a surface of the component, detecting a set of reflected light waves from the surface of the component, and producing a reflectivity data set in response to the set of reflected light waves; and a microprocessor structured to apply a fuzzy logic algorithm to the reflectivity signal to determine a solution set and produce a grain structure characterization in response to the solution set.

20 Claims, 4 Drawing Sheets

(56) References Cited

U.S. PATENT DOCUMENTS

| | | |
|---|---|---|
| 2003/0016856 A1 | 1/2003 | Walker et al. |
| 2003/0038932 A1 | 2/2003 | Weinecke et al. |
| 2004/0083024 A1* | 4/2004 | Wang .................. 700/195 |
| 2005/0036135 A1 | 2/2005 | Earthman et al. |
| 2005/0201611 A1* | 9/2005 | Lloyd et al. ............ 382/152 |
| 2006/0078193 A1 | 4/2006 | Brummel et al. |
| 2007/0217672 A1 | 9/2007 | Shannon et al. |
| 2008/0151262 A1* | 6/2008 | Tanaka et al. ............ 356/601 |
| 2008/0282972 A1 | 11/2008 | D'Souza et al. |
| 2009/0033947 A1 | 2/2009 | Boyer et al. |
| 2009/0066939 A1 | 3/2009 | Venkatachalam et al. |
| 2010/0172567 A1 | 7/2010 | Prokoski |
| 2010/0207040 A1* | 8/2010 | Tanaka et al. ............ 250/492.2 |

\* cited by examiner

INTELLIGENT AIRFOIL COMPONENT GRAIN DEFECT INSPECTION

CROSS REFERENCE TO RELATED APPLICATIONS

The present application claims the benefit of U.S. Provisional Patent Application 61/451,038, filed Mar. 9, 2011, and is incorporated herein by reference. This application also incorporates by reference, in their entirety, the following concurrently filed applications: INTELLIGENT AIRFOIL COMPONENT SURFACE IMAGING INSPECTION, U.S. Ser. No. 13/416,315; INTELLIGENT AIRFOIL COMPONENT SURFACE INSPECTION, U.S. Ser. No. 13/416,409; AUTOMATED OBJECT MANIPULATION SYSTEM, U.S. Ser. No. 13/416,705; PROTOCOL-BASED INSPECTION SYSTEM, U.S. Ser. No. 13/416,610; and ILLUMINATION SYSTEM WITH ILLUMINATION SHIELD, U.S. Ser. No. 13/416,770.

TECHNICAL FIELD

The present invention generally relates to grain structure characterization processes, and more particularly, but not exclusively, to an automated grain structure characterization process including fuzzy logic analysis.

BACKGROUND

Present approaches to grain structure characterization processes suffer from a variety of drawbacks, limitations, disadvantages and problems including those respecting efficiency, repeatability and others. There is a need for the unique and inventive grain structure characterization apparatuses, systems and methods disclosed herein.

SUMMARY

One embodiment of the present invention is a unique grain structure characterization process. Other embodiments include apparatuses, systems, devices, hardware, methods, and combinations for an automated grain structure characterization process including fuzzy logic analysis. Further embodiments, forms, features, aspects, benefits, and advantages of the present application shall become apparent from the description and figures provided herewith.

DETAILED DESCRIPTION OF THE ILLUSTRATIVE EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 1:
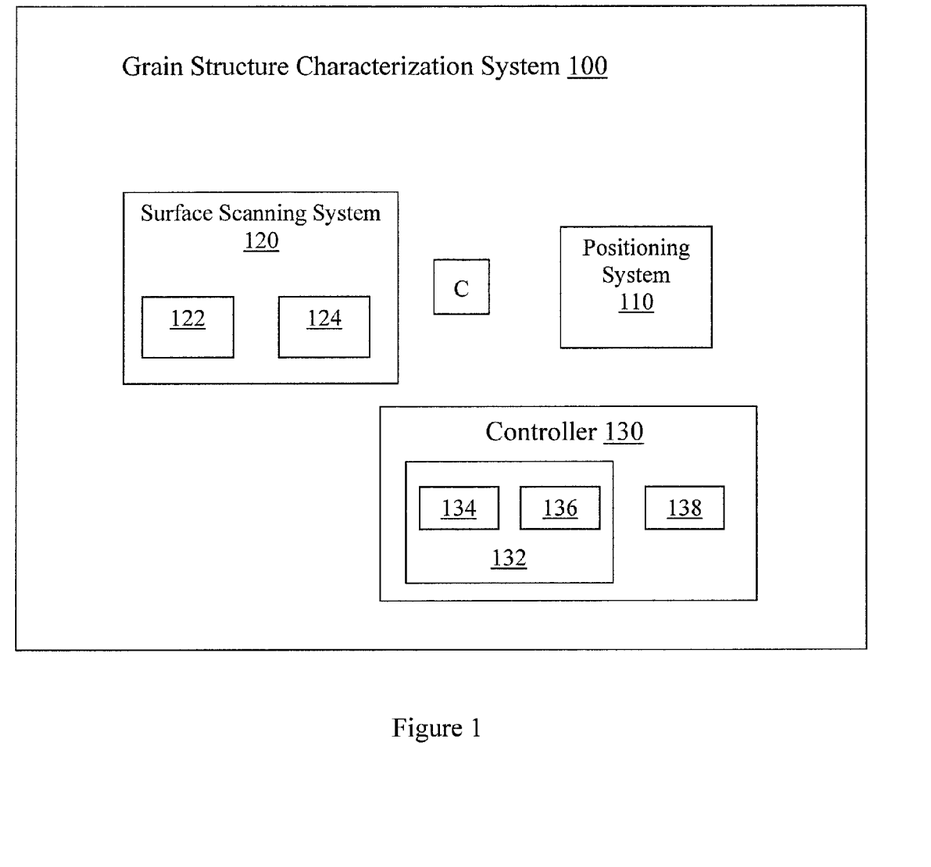
FIG. 1 is an illustration of one embodiment of a grain structure characterization system.

With reference to FIG. 1, an illustration is shown for a grain structure characterization system 100 representing an embodiment of the present application including an inspection process, algorithms, sensors, robotic positioning and analysis to locate, evaluate and report grain structures. Grain structure characterization system 100 is shown to include a positioning system 110, a surface scanning system 120 and a controller 130.

Positioning system 110 of this embodiment operates with a component presentation technique based on an algorithm for manipulating a component C with respect to surface scanning system 120 in an efficient manner with minimum hunting for component surfaces and anomalies. In various embodiments, the positioning algorithm can be provided or can be selected based on other presented parameters designated to identify the type of component being characterized. Presented parameters could include a part number, a geometry or geometrical feature, a weight, and the like. Embodiments of positioning system 110 can include a robotic component manipulator. In one particular embodiment, positioning system 110 utilizes an imaging system to identify the type of component being characterized and determines a positioning algorithm with which to provide predetermined component manipulation during characterization. Robotic component manipulation can provide consistent positioning of components, such as component C and camera or vision system, during the characterization process which can reduce variation and improve efficiency of the characterization process. In some embodiments, component manipulation can include presenting the component to a scanning device such as but not limited to a camera.

Surface scanning system 120, as shown in the embodiment of FIG. 1, includes a light source 122 and a detector unit 124. In one embodiment, light source 122 includes bright field incident illumination such as but not limited to that of light microscopes in reflective mode. Light source 122 can produce illumination in a variety of wavelengths depending on the material of the component and available equipment, thus the term "light" is not limited to visible light but includes the entire electromagnetic spectrum for shorthand. In one non-limiting embodiment, light from light source 122 is directed at the component. Detector unit 124 then detects the light reflected by the surface of component C. Variations in the reflectivity data collected by detector unit 124 can be the result of differences in the reflectance of various features of the surface of component C.

The direction of reflected light can be determined by several factors including but not limited to surface topography and grain structure. Surface topography can include surface variations resulting from voids, grain boundaries (with or without etching) and grain defects.

In an exemplary embodiment, a single crystal cast component can be subjected to the characterization system of the present application. The surface of the cast component can be scanned to produce a reflectivity signal. The reflectivity signal can indicate grain boundaries or multiple phases due to varying surface texture. The varying surface texture can reflect directed light differently allowing reflectivity differentiation between the phases.

Most materials reflect under bright field incident illumination with specular reflection where the reflected light is strongest in a single direction. Specular reflection follows the physical principle where the angle of incidence equals the angle of reflection. The angle of incidence and the angle of reflection are determined from a plane normal to the reflecting surface. As the normal plane changes direction with variations in the reflecting surface, the angle of incidence and angle of reflection change accordingly. Surfaces with different normal planes will reflect light differently. In some applications, the component to be inspected includes one or more polished surfaces and/or as-cast surfaces that uniformly reflect light and otherwise not show contrast. The surface of such a component can be prepared such as, but not limited to, chemical etching to optically enhance microstructural features so as to not uniformly reflect light and otherwise show image contrast.

Defects in the grain structure of a single crystal component can be characterized by an embodiment of the present application. Various grain defects can find their way into a single crystal manufacturing process such as but not limited to high angle grain boundaries, low angle grain boundaries, recrystallized grains, and twinning defects. Examples of defects can include precipitates, dislocations and impurities. One embodiment of the present application is designed to automatically locate, evaluate and report grain defects on families of single crystal cast airfoil type components. Embodiments disclosed herein can also generate a report of the sizes and the locations of the grain defects on the component. One embodiment of the present application includes identifying defects, defect locations and defect density.

Controller 130 of grain structure characterization system 100 is shown schematically in the embodiment of FIG. 1 as a single component containing modules capable of performing various functions. Each function can be located on the same or separate pieces of hardware and can be one of several hardware varieties available and arranged by one skilled in the art. Controller 130 can also include one or more microprocessors where a single microprocessor provides the functions of each module or separate microprocessors are used for one or more of the control modules.

Controller 130 as shown in FIG. 1 is capable of operating a scanned data processing module 132 and a robotic manipulation module 138. Robotic manipulation module 138 is shown in FIG. 1 as part of controller 130. Robotic manipulation module 138 can be part of the positioning equipment in positioning system 124 as a single system or as separate components. For one specific embodiment, robotic manipulation module 138 is capable of providing a positioning algorithm and predetermined part manipulation instructions to positioning system 110 in response to an identification of component C.

Scanned data processing system 132 can include an analyzer module 134 and a scanning module 136. In one embodiment, scanning module 136 can interact with surface scanning system 120 to provide equipment controls as an alternative to controls provided directly with the scanning system equipment or from another source and can be capable of providing acquisition and manipulation capabilities for data sets provided to surface scanning system 120.

In one form, analyzer module 134 can be a fuzzy logic analyzer module capable of providing analysis of the scanned data sets from surface scanning system 120. Fuzzy logic can be used in grain structure characterization system 100 to deal with fuzzy concepts—concepts that cannot be expressed as "true" or "false" but rather as "partial truths."

In an automated grain structure characterization system, a reflectivity analysis method in an embodiment of the present application can include fuzzy logic analysis to enable the system to use an analysis tool with appropriate processing times for part inspection. In general, a fuzzy logic analysis system is a logic analysis system operable to process data by replacing what are commonly Boolean logic rules with a collection of fuzzy membership functions and rules. An example rule in a fuzzy logic system may be of the form:

If x is low and y is high, then z is low, where x and y are input variables, z is an output variable, "low" is a membership function defined on x and z, and "high" is a membership function defined on y.

The rule's premise describes the degree to which the rule applies, while the rule's consequent assigns a membership function to the output variable(s), where the set of rules in a fuzzy logic analysis system is known as the rule base or knowledge base.

Because fuzzy logic is a mathematical model for addressing inherently imprecise data, a fuzzy logic analysis can be applied to the present application. For example, the concept of 'brightness' is not mathematically expressed in an equation. Luminescence may be a quantity but 'brightness' is not. A sharp cut off does not exist between 'bright' and 'not bright.' One cannot say that 'bright' is at X luminescence but 'not bright' is at X−1 luminescence.

An operator is able to detect differing 'reflectivity' for a sample. How much 'reflectivity' observed will vary between operators leading to the reduced repeatability in component characterization. Fuzzy logic provides a mathematical model of the vagueness found in non-precise measurements of reflectivity allowing automated determinations regarding component analysis such as grain structure characterization.

Figure 2:
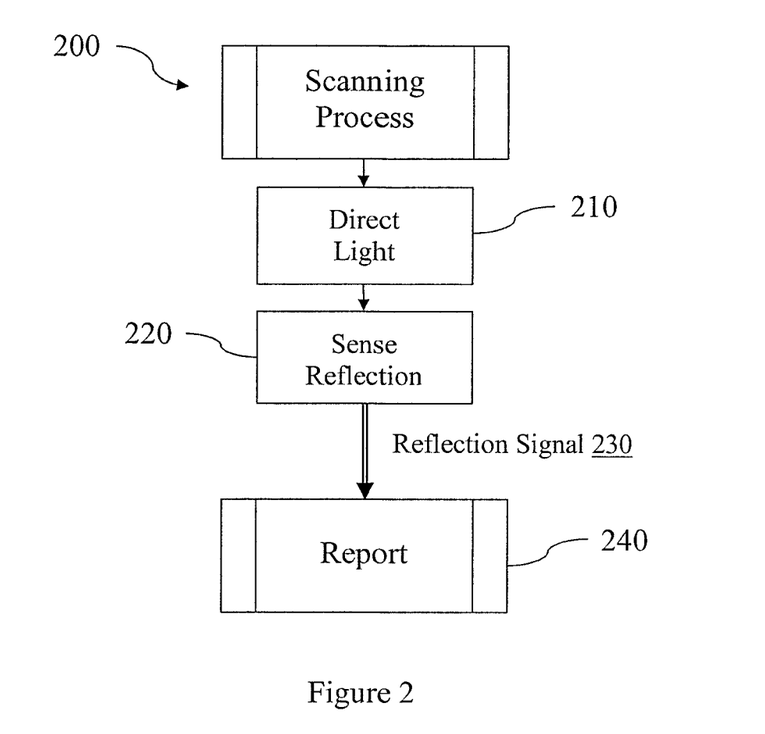
FIG. 2 is a flow diagram of one embodiment of a grain structure characterization process.

FIG. 2 shows a flow diagram of an embodiment of the present application including a scanning process 200. Scanning process 200 begins with operation 210 where light is directed at a localized area of a component's surface. Operation 210 may utilize light source 122 from FIG. 1. In response to operation 210, operation 220 senses the light which is reflected by the component surface. Operation 220 may be accomplished with detection unit 124 from FIG. 1 to detect the reflected light over a specified range of angles. A reflection signal 230 representing the intensity of the reflected light is provided for a reporting operation 240. Operation 240 may include further analysis regarding the reflected light intensity resulting in a characterization of the component surface. Analysis from operation 240 can include fuzzy logic analysis. In an embodiment of the present application, grain structure characterization of a component surface as part of operation 240 may include defect inspection of a single crystal airfoil casting.

Figure 3:
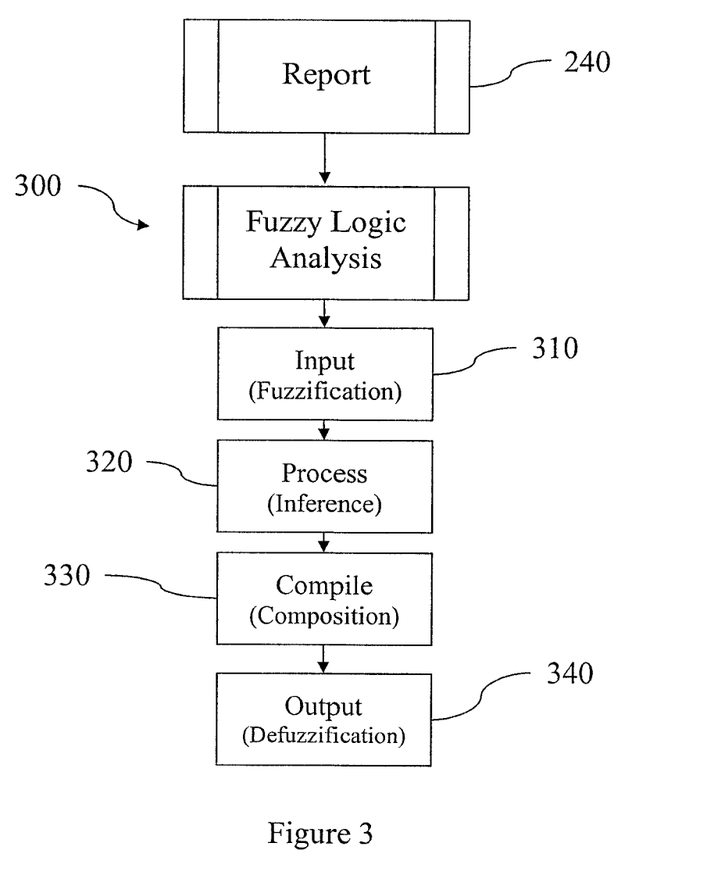
FIG. 3 is a flow diagram of a characterization process from FIG. 2.

FIG. 3 shows an embodiment of a fuzzy logic analysis that can be part of reporting operation 240 from FIG. 2. Data processing in a fuzzy logic analysis system of an embodiment of the present application can include four high level steps that correspond roughly to an input stage 310, a processing stage 320, a compilation stage 330 and an output stage 340. These operations can be described in slightly differing terms and can be combined, expanded or omitted based on the way the fuzzy logic analysis is described without changing the meaning or intent of using fuzzy logic in this embodiment of the present application.

1. Input Stage 310—Fuzzification: The membership functions defined for the input variables can be applied to the actual values of the input variables to determine the degree of truth for each rule premise. The input variables in a fuzzy control system are in general mapped into sets of membership functions known as "fuzzy sets" in the process of converting an input value to a fuzzy value. All the rules that apply can be invoked, using the membership functions and truth values obtained from the inputs, to determine the results of the rules.

2. Processing stage 320—Inference: The truth value for the premise of each rule can be computed and applied to its consequent. This computation results in one fuzzy subset being assigned to each output variable. The computation result in turn can be mapped into a membership function and truth value controlling the output variable.
3. Compilation stage 330—Composition: All of the fuzzy subsets assigned to each output variable can be combined together to form a single fuzzy output subset for each output variable.
4. Output stage 340—Defuzzification: The fuzzy output subset for each output variable can be convertible to a unique solution or a 'crisp' answer.

In a specific embodiment, a grain structure characterization system of the present application utilizes fuzzy logic analysis to determine grain defects of a component. The characterization system presents a surface of the component to a scanning system by manipulating the component according to a positioning algorithm. The scanning system produces a reflectivity data set as a result of light directed to the surface of the component reflecting back. The reflectivity data set would include the intensity of reflecting light and location on the surface of the component. Fuzzy logic analysis is applied where the reflectivity data set is collected as the input variables. The input variables are assigned a degree of intensity. The degree of intensity is compiled to produce an output data set related to the level of reflectivity and location. The output data set can be characterized to indicate grain structure or, more specifically, grain defects. Characterization can be performed by comparing the output data set to standard data sets in an airfoil defect knowledge bank.

Figure 4:
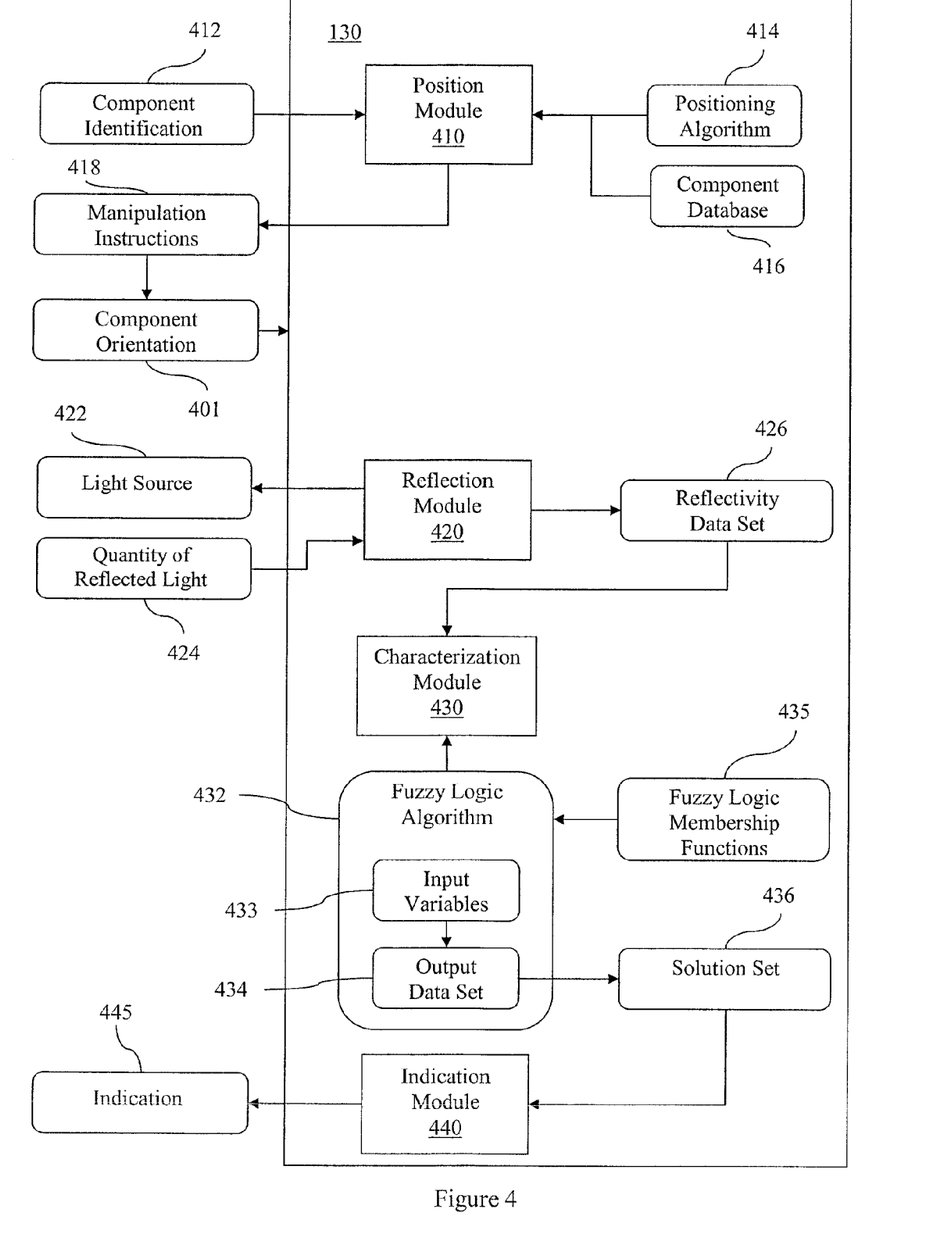
FIG. 4 is a diagram illustrating one embodiment of a characterization system of the present application.

Referencing FIG. 4, one embodiment of an apparatus includes a controller 130 with various components illustrated as representative modules, inputs, outputs and intermediate data parameters. Module 410 is a position module structured to determine a positioning algorithm 414 in response to the identification of a type of component 412 and a component positioning database 416. Various systems can be available for identifying the component in component identification 412 such as but not limited to bar code, scan, operator input, CMM data, imaging data and the like.

Component manipulation instructions 418 for the positioning equipment are provided in response to positioning algorithm 414. Manipulation instructions 418 provides a component orientation data set 401. In one embodiment, manipulation instructions 418 can provide robotic manipulation of the component during grain structure characterization process 100.

Module 420 is a reflection module structured to direct a source of light 422 on to the surface of a component and detect a quantity of reflected light 424 with a detection unit. Module 420 is further structured to provide a reflectivity data set 426 in response to the quantity of reflected light 424. Module 430 is a characterization module where a fuzzy logic algorithm 432 can be applied to the reflectivity data set. Fuzzy logic algorithm 432 applies reflectivity data set 426 to a set of input variables 433. A set of fuzzy logic membership functions 435 assigns a degree of intensity to the set of input variables 433. Fuzzy logic algorithm 432 determines an output data set 434 which is converted into a solution set 436. Indication module 440 is structured to identify an indication 445 of a grain structure feature in response to solution set 436 and can also be in response to component orientation data set 401.

Grain structure features indicated by a grain structure characterization system as part of an embodiment of the present application can include but are not limited to grain structure, grain defects, grain locations, grain size, and grain defect density. In some embodiments the part can include a single crystal, a directionally solidified, and/or an equiaxed grain structure. In a further embodiment the part can include an airfoil component of a gas turbine engine. One embodiment of a grain structure characterization system can operate to mechanically locate, evaluate, and report grain structure characterization features on families of airfoil type components. Another embodiment of the system can generate a report of the sizes, locations and types of grain structures of the component in tabular or graphical form.

An embodiment of the present application applies a special lighting configuration, a part presentation technique, and a fuzzy logic based processing technique for identifying grain structures in a single crystal cast airfoil component. Yet another embodiment can include an algorithm for manipulating a part with respect to lighting and sensing positions in an efficient manner with minimum hunting and a fuzzy logic based processing algorithm to identify grain structure features which can indicate a microstructural defect. Embodiments of the present application can be applied to components requiring grain defect inspection such as but not limited to single crystal cast components, directionally solidified cast components, and equiax solidified cast components.

In one embodiment of the present application, a method includes applying a grain structure characterization process to a component, applying an algorithm to efficiently position the component with an automatic positioning algorithm and applying fuzzy logic analysis to identify grain structure characterizations of the component.

One aspect of the present application is a system including a component manipulator structured to position a component in response to a positioning algorithm; a surface scanner capable of producing a set of light waves directed at a surface of the component, detecting a set of reflected light waves from the surface of the component, and producing a reflectivity signal in response to the set of reflected light waves; and a microprocessor structured to apply a fuzzy logic algorithm to the reflectivity signal to determine a solution set in response to the reflectivity signal and produce a grain structure characterization in response to the solution set. Further features of the grain structure characterization can include a pass/fail signal, a characterization report and an indication of a grain structure selected from a group consisting of grain structure, grain defects, grain locations, grain size, grain defect density and combinations thereof.

Another aspect of the present application is a method including applying a positioning algorithm to manipulate at least one piece of positioning equipment in response to a component; analyzing a surface of the component with a light source and a reflectivity detection unit; producing a reflectivity data set in response to analyzing the surface of the component; applying a fuzzy logic analysis to the reflectivity data set where the fuzzy logic analysis is capable of producing a solution data set; and providing a grain structure characterization in response to the solution data set. Further features of the fuzzy logic analysis can include an input collecting module, a processing module, a compiling module, and an output producing module where the input collecting module includes collecting the reflectivity data set and the output producing module includes producing the solution data set. A further feature of the at least one piece of positioning equipment can include a robotic manipulator capable of positioning the component in response to the component and the positioning algorithm. Further features of the grain structure characterization can include a pass/fail signal, a characterization report and an indication of a grain structure selected from a group consisting of grain structure, grain defects, grain locations, grain size, grain defect density and combinations thereof.

Yet another aspect of the present application is an apparatus including a position module structured to position a component; a reflection module structured to provide a light source directed to a surface of the component, a detection unit to detect a quantity of reflected light from the surface of the component and a reflectivity data set in response to the quantity of reflected light; a characterization module utilizing a fuzzy logic algorithm capable of applying the reflectivity data set as a set of input variables, assigning a degree of intensity to the set of input variables, determining an output data set and converting the output data set to a set of solutions; and an indication module structured to provide at least one indication in response to the set of solutions.

Features of this aspect can include the at least one indication providing a characterization of at least one grain defect, a pass/fail signal, a characterization report and an indication of a grain structure selected from a group consisting of grain structure, grain defects, grain locations, grain size, grain defect density and combinations thereof. Further features of the at least one indication can include a grain structure characterization in response to the set of solutions with a cognitive characterization process utilizing an airfoil defect knowledge bank. Further features of the position module can include a component manipulator where the component manipulator positions the component in response to a positioning algorithm, utilizes an imaging system to identify a component type of the component and determines the positioning algorithm in response to the component type, and identifies the component in response to the reflectivity data set and a component orientation database.

One aspect of the present application is a system including a component manipulator structured to position a component in response to a positioning algorithm; a surface scanner capable of producing an electromagnetic radiation directed at a surface of the component, detecting the electromagnetic radiation from the surface of the component, and producing a reflectivity signal in response to the electromagnetic radiation; and a processor structured to apply a fuzzy logic algorithm to the reflectivity signal to determine a solution set in response to the reflectivity signal and produce a grain structure characterization in response to the solution set. Further features of the grain structure characterization can include a pass/fail signal, a characterization report and an indication of a grain structure selected from a group consisting of grain structure, grain defects, grain locations, grain size, grain defect density and combinations thereof.

Yet another aspect of the present application is an apparatus including a position module structured to position a component; a reflection module structured to provide a light source directed to a surface of the component, a detection unit to detect a quantity of reflected light from the surface of the component and a reflectivity data set in response to the quantity of reflected light; a characterization module utilizing a fuzzy logic algorithm capable of applying the reflectivity data set as a set of input variables, assigning a degree of intensity to the set of input variables, determining an output data set and converting the output data set to a set of solutions; and an indication module structured to provide at least one indication of a grain structure in response to the set of solutions.

Features of this aspect can include the at least one indication providing a characterization of at least one grain defect, a pass/fail signal, a characterization report and an indication of a grain structure selected from a group consisting of grain structure, grain defects, grain locations, grain size, grain defect density and combinations thereof. Further features of the at least one indication can include a grain structure characterization in response to the set of solutions with a cognitive characterization process utilizing an airfoil defect knowledge bank. Further features of the position module can include a component manipulator where the component manipulator positions the component in response to a positioning algorithm, utilizes an imaging system to identify a component type of the component and determines the positioning algorithm in response to the component type, and identifies the component in response to the reflectivity data set and a component orientation database.

While the invention has been illustrated and described in detail in the drawings and foregoing description, the same is to be considered as illustrative and not restrictive in character, it being understood that only the preferred embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A system comprising:
   a component manipulator structured to position a component in response to a positioning algorithm;
   a surface scanner configured to:
      output electromagnetic radiation directed at a surface of the component,
      detect reflected electromagnetic radiation from the surface of the component, and
      produce a reflectivity signal in response to detecting the reflected electromagnetic radiation; and
   a processor configured to:
      apply a fuzzy logic algorithm to the reflectivity signal to determine a solution set in response to the reflectivity signal; and
      produce a grain structure characterization in response to the solution set.

2. The system of claim 1, wherein the processor is configured to produce a grain structure characterization including a pass/fail signal, and wherein the electromagnetic radiation is a visible or near-visible light.

3. The system of claim 1, wherein the processor is configured to produce a grain structure characterization including a characterization report.

4. The system of claim 1, wherein the processor is configured to produce a grain structure characterization including a feature selected from the group consisting of: grain structure, grain defects, grain locations, grain size, grain defect density and combinations thereof.

5. A method comprising:
   applying a positioning algorithm to manipulate at least one piece of positioning equipment to position a component;
   outputting electromagnetic radiation directed at a surface of the component;

detecting reflected electromagnetic radiation from the surface of the component;
producing a reflectivity data set in response to detecting the reflected electromagnetic radiation;
applying a fuzzy logic analysis to the reflectivity data set to produce a solution data set; and
producing a grain structure characterization in response to the solution data set.

6. The method of claim 5, wherein the fuzzy logic analysis includes an input collecting module, a processing module, a compiling module, and an output producing module.

7. The method of claim 6, wherein the input collecting module includes collecting the reflectivity data set.

8. The method of claim 6, wherein the output producing module includes producing the solution data set.

9. The method of claim 5, wherein the at least one piece of positioning equipment includes a robotic manipulator.

10. The method of claim 5, wherein producing the grain structure characterization comprises indicating a grain structure feature selected from the group consisting of grain structure, grain defects, grain locations, grain size, grain defect density and combinations thereof.

11. The method of claim 10, wherein producing the grain structure characterization comprises producing a pass/fail signal.

12. The method of claim 10, wherein producing the grain structure characterization comprises producing a characterization report.

13. An apparatus comprising:
a controller comprising:
 a position module that determines a positioning algorithm used to position a component;
 a reflection module that
  controls a light source to direct light to a surface of the component,
  control a detection unit to detect a quantity of reflected light from the surface of the component, and
  generates reflectivity data set in response to the quantity of reflected light;
 a grain structure characterization module utilizing a fuzzy logic algorithm to:
  apply the reflectivity data set as a set of input variables;
  assign a degree of intensity to the set of input variables;
  determine an output data set; and
  convert the output data set to a set of solutions; and
 an indication module that output at least one indication of a grain structure in response to the set of solutions.

14. The apparatus of claim 13, wherein the indication module outputs the at least one indication by at least outputting a characterization of at least one grain defect.

15. The apparatus of claim 13, wherein the indication module outputs the at least one indication by at least outputting a grain structure feature selected from the group consisting of: grain structure, grain defects, grain locations, grain size, grain defect density and combinations thereof.

16. The apparatus of claim 13, wherein the indication module outputs the at least one indication by at least outputting a grain structure characterization in response to the set of solutions and a cognitive characterization process utilizing an airfoil defect knowledge bank.

17. The apparatus of claim 13, wherein the position module controls a component manipulator to position the component in response to a positioning algorithm.

18. The apparatus of claim 17, wherein the component manipulator utilizes an imaging system to identify a component type of the component, and wherein the position module determines the positioning algorithm in response to receiving an indication of the component type.

19. The apparatus of claim 17, wherein the positioning module identifies the component in response to the reflectivity data set and a component orientation database.

20. The apparatus of claim 13, wherein the component comprises a single crystal cast airfoil-type component.

* * * * *